United States Patent
Geitz et al.

(10) Patent No.: US 9,321,216 B2
(45) Date of Patent: *Apr. 26, 2016

(54) COMPOSITE EPTFE-SILICONE COVERING FOR STENT

(71) Applicant: Boston Scientific Scimed, Inc., Maple Grove, MN (US)

(72) Inventors: Kurt A. Geitz, Sudbury, MA (US); Paul K. Norton, Lunenburg, MA (US); Michael Madden, Temple, NH (US); Ralph J. Barry, Jr., Hudson, MA (US); Claude O. Clerc, Marlborough, MA (US); Gerald Fredrickson, Westford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 30 days.

This patent is subject to a terminal disclaimer.

(21) Appl. No.: 14/547,617

(22) Filed: Nov. 19, 2014

(65) Prior Publication Data

US 2015/0068676 A1 Mar. 12, 2015

Related U.S. Application Data

(63) Continuation of application No. 13/335,637, filed on Dec. 22, 2011.

(60) Provisional application No. 61/427,785, filed on Dec. 28, 2010.

(51) Int. Cl.
| | |
|---|---|
| *B29C 69/00* | (2006.01) |
| *A61L 31/10* | (2006.01) |
| *B29C 41/08* | (2006.01) |
| *B29C 70/70* | (2006.01) |
| *B29K 83/00* | (2006.01) |
| *B29K 627/18* | (2006.01) |
| *B29L 31/00* | (2006.01) |
| *B29K 21/00* | (2006.01) |

(52) U.S. Cl.
CPC .............. *B29C 69/00* (2013.01); *A61L 31/10* (2013.01); *B29C 41/085* (2013.01); *B29C 70/70* (2013.01); *B29K 2021/00* (2013.01); *B29K 2083/00* (2013.01); *B29K 2627/18* (2013.01); *B29L 2031/753* (2013.01); *B29L 2031/758* (2013.01)

(58) Field of Classification Search
CPC ....... A61F 2/07; A61F 2/90; A61F 2240/001; B29L 2023/00; B29L 2023/007; Y10S 623/901
USPC .............. 623/1.13, 1.46, 1.15, 23.7; 156/280; 427/2.28
See application file for complete search history.

(56) References Cited

U.S. PATENT DOCUMENTS

| | | | | |
|---|---|---|---|---|
| 4,955,899 | A * | 9/1990 | Della Corna et al. | 623/1.46 |
| 7,560,006 | B2 | 7/2009 | Rakos et al. | |
| 2004/0024442 | A1* | 2/2004 | Sowinski et al. | 623/1.13 |
| 2005/0255230 | A1* | 11/2005 | Clerc et al. | 427/2.1 |
| 2006/0088653 | A1 | 4/2006 | Chappa | |

* cited by examiner

*Primary Examiner* — Michael N Orlando
*Assistant Examiner* — Margaret Squalls
(74) *Attorney, Agent, or Firm* — Seager, Tufte & Wickhem, LLP (57) ABSTRACT

A medical device consists of a stent having a first surface and a second surface parallel to the first surface; a single expanded polytetrafluoroethylene (ePTFE) layer contacting the first surface of the stent; and an elastomeric layer applied to at least one surface of the stent. In at least one embodiment, the elastomeric layer is silicone. In at least one embodiment, the medical device is manufactured by positioning the ePTFE layer such that a first surface of the ePTFE layer contacts a first surface of the stent to form a stent-ePTFE assembly; and applying an elastomeric solution to the first surface of the ePTFE layer and at least one surface of the stent.

20 Claims, 5 Drawing Sheets

COMPOSITE EPTFE-SILICONE COVERING FOR STENT

CROSS REFERENCE TO RELATED APPLICATIONS

This application is a Continuation of U.S. patent application Ser. No. 13/335,637, filed Dec. 22, 2011, which claims the benefit of U.S. Provisional Application No. 61/427,785, filed Dec. 28, 2010, the contents of which are hereby incorporated by reference.

BACKGROUND OF THE INVENTION

This invention relates generally to implantable endoprostheses such as stent-grafts and other similar devices. Such implantable endoprostheses are well known in the art for the treatment and repair of various bodily lumens, such as vessels in the vascular system, the gastrointestinal system, the airway, and other applications in the body.

A stent is a generally longitudinal tubular device formed of biocompatible material which is useful to open and support various lumens in the body. Stents generally are radially expanded so as to support and reinforce the vessel. Radial expansion of the stent may be accomplished by inflation of a balloon attached to the catheter or the stent may be a self-expanding stent, which will radially expand once deployed, or a combination of the two.

Grafts are tubular devices which may be formed of a variety of material, including textiles, and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels.

A stent and a graft may be combined into a stent-graft endoprosthesis to combine the features and advantages of each. For example, tubular coverings have been provided on the inner and/or outer surfaces of stents to form the stent-graft. Such covered stents or stent-grafts have many applications, but are typically used to prevent stent obstruction due to tumor or tissue ingrowth. Previously, covered stents have been manufactured by placing the stent between two ePTFE sleeves or grafts and fusing the two sleeves together by applying heat and pressure.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §1.72.

BRIEF SUMMARY OF THE INVENTION

The present invention is a medical device for use in a bodily lumen, including a variety of gastrointestinal, airway, vascular, and other applications. In at least one embodiment, the medical device includes a stent having a first surface and a second surface parallel to the first surface; a single expanded polytetrafluoroethylene (ePTFE) layer contacting the first surface of the stent; and an elastomeric layer between the single ePTFE layer and the first surface of the stent. In at least one embodiment, the elastomeric layer comprises silicone.

In at least one embodiment, the first surface is an inner surface of the stent, and the second surface is an outer surface of the stent. The single ePTFE layer has an outer surface that contacts the inner surface of the stent. In at least one embodiment, the first surface is an outer surface of the stent and the second surface is an inner surface of the stent. The single ePTFE layer has an inner surface that contacts the outer surface of the stent.

A method of manufacturing a medical device is also provided. The method comprises the steps of positioning a single ePTFE layer such that a first surface of the ePTFE layer contacts a first surface of the stent to form a stent-ePTFE assembly; and applying an elastomeric solution to the first surface of the ePTFE layer and at least one surface of the stent.

In at least one embodiment, the elastomeric solution is applied by dipping the stent-ePTFE assembly into the elastomeric solution.

In at least one embodiment, the elastomeric solution is sprayed onto the stent-ePTFE assembly using a spray system. In at least one embodiment, the spray system comprises: a syringe loaded with the elastomeric solution; a gas supply; and a nozzle connected to the syringe with a first tube. In at least one embodiment, the nozzle is also connected to the gas supply with a second tube. In at least one embodiment, the elastomeric solution is mixed with the gas in the nozzle to form a spray. In at least one embodiment, while the elastomeric solution is being sprayed onto the stent-ePTFE assembly, the stent-ePTFE assembly is maneuvered relative to the nozzle by rotation, translation, or both.

In at least one embodiment, the stent-ePTFE assembly is placed into a tube having an injection port. In at least one embodiment, the elastomeric solution is applied by injecting the elastomeric solution into the tube through the injection port.

In some embodiments, at least one of the stent and the ePTFE layer is placed onto a mandrel. In at least one embodiment, the mandrel is a balloon. In at least one embodiment, the balloon is positioned in a lumen of at least one of the stent or the ePTFE layer. In at least one embodiment, the balloon is then inflated until the balloon conforms to the shape of at least the stent or the ePTFE layer before the elastomeric solution is applied. In at least one embodiment, the balloon is deflated and removed from the lumen after the applied elastomeric solution is cured.

DETAILED DESCRIPTION OF THE INVENTION

Medical devices comprising a stent, an elastomeric coating, and at least one ePTFE layer are known in the art, as described, for example, in U.S. Pat. No. 6,488,701 and US Patent Publication Nos. 2004/0049264, 2004/0162604, 2009/0192627 and 2009/0319034, each of which is incorporated herein by reference in its entirety.

Figure 1:
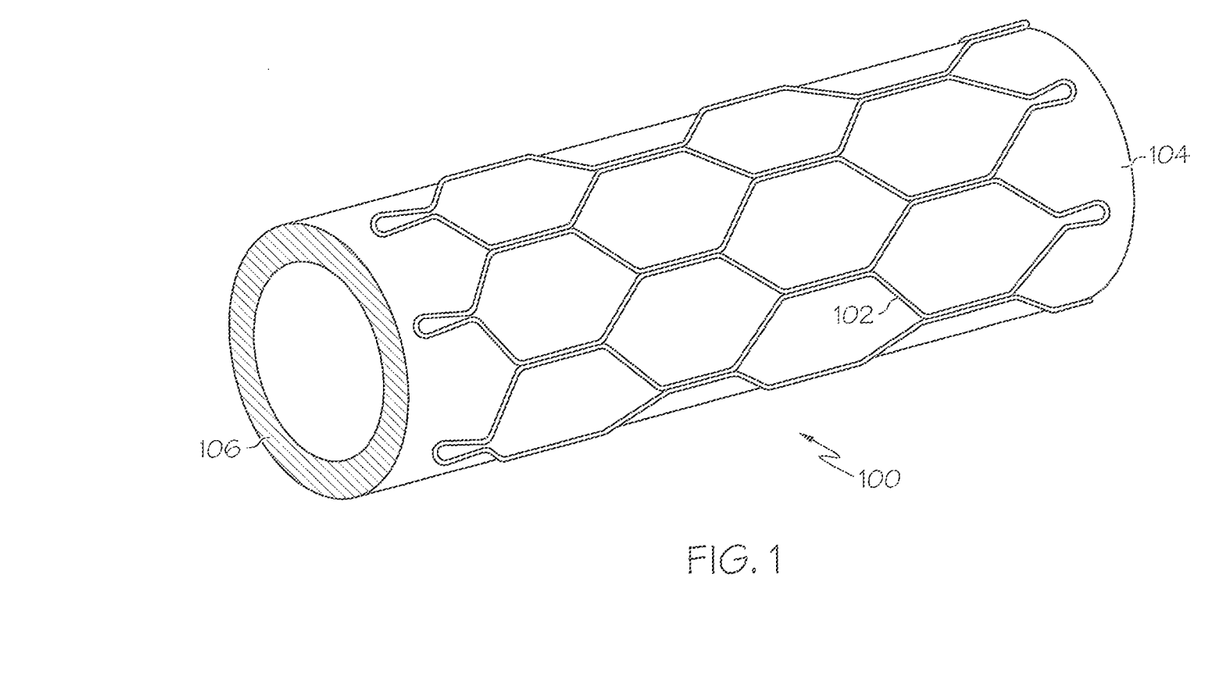
FIG. 1 is a perspective view an embodiment of the present invention.

FIG. 1 shows a perspective view of a medical device 100, such as an endoprosthesis or stent-graft. As shown in FIG. 1, medical device 100 consists of a stent 102, an elastomeric layer 104, and a single layer of expanded polytetrafluoroethylene (ePTFE) 106. In at least one embodiment, the elastomeric layer 104 comprises silicone. In some embodiments of the present invention, the elastomeric layer 104 is located between the stent 102 and the single ePTFE layer 106. In some embodiments, the elastomeric layer adheres the single ePTFE layer 106 to the stent 102. In some embodiments, the elastomeric layer 104 fills any gaps or space between the stent 102 and the single ePTFE layer 106. Where the medical device 100 needs to be removed after placement in the body, the single ePTFE layer 106 adds structural reinforcement, which makes the medical device 100 easier to remove from a vessel without damaging the stent 102.

In some embodiments, the stent 102 is a balloon expandable stent, a self-expanding stent or a hybrid expandable stent. In some embodiments, the stent 102 can be a laser cut stent or can be woven, braided, bent, twisted, knotted, laser cut, molded, tied, and/or wrapped from one or several filaments into a desired configuration. In some embodiments, the stent 102 can include at least one flare, at least one taper and/or at least one side branch. In some embodiments, the stent 102 has a constant diameter along a length of the stent. In other embodiments, the stent 102 has a non-constant diameter along the length of the stent. In some embodiments, the stent can be a bifurcated stent. In some embodiments, the stent can comprise mono-filament or multiple filament wires of any cross-section. In some embodiments, the stent 102 can comprise metals, polymers and combinations thereof.

In at least one embodiment, the elastomeric layer 104 includes an elastomer such as silicone. In some embodiments, the elastomeric layer 104 includes other elastomeric polymers, such as polystyrene-polyisobutylene-polystyrene triblock copolymer (SIBS), polyurethane, and other comparable elastomeric polymers. In some embodiments, the elastomeric layer 104 includes radiopaque particles.

In at least one embodiment, a portion of medical device 100 can be coated with at least one therapeutic agent. In some embodiments, the entire medical device 100 is coated with a therapeutic agent. In some embodiments, the stent 102 is coated with a therapeutic agent. In some embodiments, the ePTFE layer 106 is coated with a therapeutic agent. In some embodiments, both the stent and the ePTFE layer are coated with a therapeutic agent. In some embodiments, the elastomeric layer 104 contains a therapeutic agent. It is relatively convenient to mix a therapeutic agent with the elastomer and apply them simultaneously to the ePTFE layer or stent as elastomeric layer 104. The elastomers also can help release the therapeutic agent. In some embodiments, combining the elastomeric layer with the therapeutic agent provides a mechanism for timed release of the therapeutic agent as opposed to a burst release.

In any of these embodiments, the therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may include but is not limited to: polystyrene-polyisobutylene-polystyrene triblock copolymer (SIBS), polyethylene oxide, silicone rubber and/or any other suitable substrate. The therapeutic agent can also have antimicrobial activity, such as silver or antibiotics including, but not limited to, Rifampin, Minocycline, Polymyxin B, Tobramycin, Gentamicin and combinations thereof.

In at least one embodiment, the ePTFE layer 106 is a tubular sleeve. In at least one embodiment, the ePTFE is extruded into the tubular sleeve. In other embodiments, the ePTFE can be used in a sheet, film or tape that is helically wrapped into a cylindrical form. The ePTFE sheet, film or tape can be wrapped around the stent 102 or wrapped around a blank corresponding to the desired diameter of the ePTFE layer 106. In at least one embodiment, the ePTFE layer 106 generally conforms to the shape of the stent 102. In at least one embodiment, the ePTFE layer 106 has a thickness between about 25 microns (0.0001 in) and 500 microns (0.020 in).

In some embodiments, the ePTFE layer 106 is porous. Where the ePTFE layer 106 is porous, the elastomeric layer 104 enters the pores of the ePTFE layer 106 to create a mechanical bond between the ePTFE layer 106 and at least the elastomeric layer 104. The elastomeric layer 104 also enters the openings between struts of the stent 102 to create a mechanical bond between the stent 102 and at least the elastomeric layer 104. Other materials may be used for layer 106, such as porous PTFE and other suitable porous materials. In at least one embodiment, the mechanical bond created between the elastomeric layer and the ePTFE layer for the medical device is sufficient enough that a tie layer is not required.

In some embodiments, the ePTFE layer 106 has a node and fibril structure that allows for tissue ingrowth. The distance between the nodes is called the internodal distance. The internodal distance is linked to tissue ingrowth and neointima formation in vascular grafts. In some embodiments, the internodal distance is between about 1 micron (0.00004 inches) and 100 microns (0.004 inches), depending on the manufacturing process used. In at least one embodiment, the internodal distance is between about 20 microns (0.0008 inches) and 60 microns (0.0024 inches). In some embodiments, PTFE is expanded either uni-axially or bi-axially to form ePTFE. Where the stent 102 is a braided stent, bi-axially oriented ePTFE is preferred. Where the ePTFE is uni-axially oriented, the ePTFE can be oriented such that it aligns with either the longitudinal axis or the radial axis of the stent 102.

In some embodiments, the elastomeric layer 104 substantially covers the entirety of the ePTFE layer 106. In other embodiments, the elastomeric layer 104 covers only a portion of the ePTFE layer 106. In some embodiments where the ePTFE layer 106 is porous, the elastomeric layer 104 fills in at least a portion of at least some of the pores in the ePTFE layer 106. In some embodiments, the elastomeric layer 104 substantially covers the entirety of the stent 102. In other embodiments, the elastomeric layer 104 covers only a portion of the stent 102. In other embodiments, the elastomeric layer 104 covers only that portion of the stent 102 that is in contact with the ePTFE layer 106.

In at least one embodiment, the ePTFE layer 106 may fold about at least one end of the stent 102, such that a portion of the outer surface of the ePTFE layer 106 contacts both the inner surface of the stent 102 and the outer surface of the stent 102. In some embodiments, the ePTFE layer 106 may fold about both ends of the stent layer 102. In at least one embodiment, the amount of the ePTFE layer 106 that contacts both the inner surface of the stent layer 102 and the outer surface of the stent layer 102 is no more than about 0.2 inches (5 millimeters) at the at least one end of the medical device 100.

Figure 2:
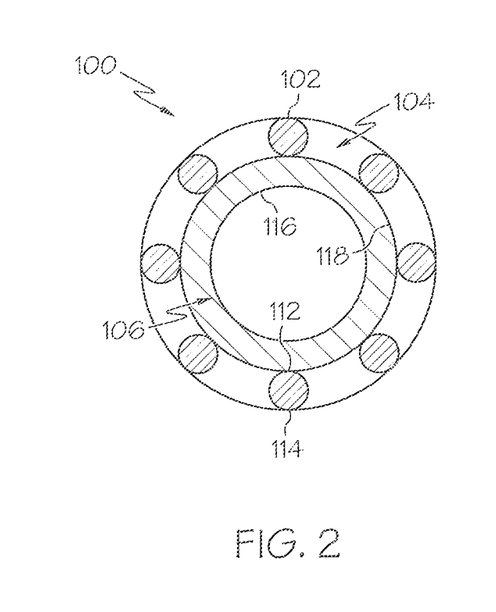
FIG. 2 is a cross-sectional view of the embodiment shown in FIG. 1.

FIG. 2 shows a cross section of the medical device 100 shown in FIG. 1. As shown in FIG. 2, stent 102 has an inner surface 112 that defines a lumen of the stent and an outer surface 114 with a thickness therebetween. FIG. 2 also shows ePTFE layer 106, which has an inner surface 116 that defines a lumen of the ePTFE layer 106, an outer surface 118, and a thickness therebetween. In at least the embodiment shown, the outer surface 118 of the ePTFE layer 106 contacts at least a portion of the inner surface 112 of stent 102. The ePTFE layer 106 is positioned within the lumen of the stent 102. The ePTFE layer 106 on the inside of the medical device 100 as shown in FIG. 2 helps encourage food and fluid passage, prevent mucus clogging, and prevent biofilm formation depending on the application of the medical device.

In at least the embodiment of FIG. 2, the elastomeric layer 104 is applied such that the elastomeric layer 104 substantially covers the stent 102. However, as described above, the elastomeric layer 104 may only be applied to a portion of the stent 102. Further, as described above with respect to some embodiments, the elastomeric layer 104 covers at least a portion of the outer surface 118 of the ePTFE layer 106. In some embodiments, the elastomeric layer 104 covers the entirety of the outer surface 118 of the ePTFE layer 106. In some embodiments, the elastomeric layer 104 covers only that portion of the outer surface 118 of the ePTFE layer 106 that is in contact with the stent 102.

Figure 3:
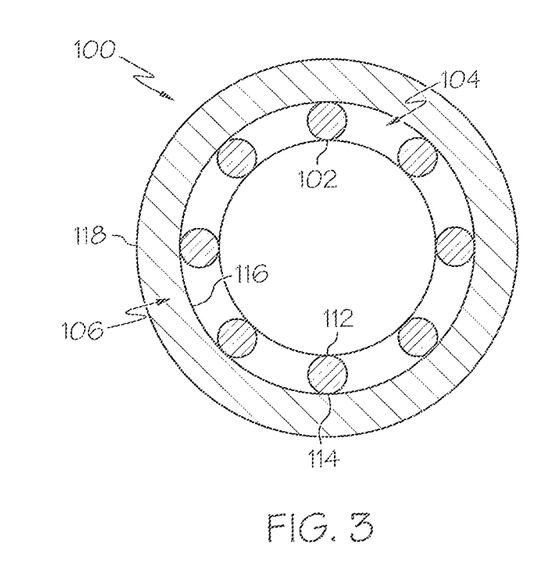
FIG. 3 is a cross-sectional view of an embodiment of the invention.

A cross section of an embodiment of the medical device 100 is shown in FIG. 3. The inner surface 116 of the ePTFE layer 106 contacts at least a portion of the outer surface 114 of the stent 102. In at least the embodiment of FIG. 3, the elastomeric layer 104 is applied such that the elastomeric layer 104 substantially covers the entirety of stent 102. However, as described above, the elastomeric layer 104 may only be applied in some embodiments to a portion of the stent 102. Having the ePTFE layer 106 on the outside surface of the stent 102 allows some amount of tissue ingrowth within the porous ePTFE structure, while the elastomeric layer 104 prevents further tissue ingrowth, especially in those embodiments where the elastomeric layer includes silicone. Such tissue ingrowth will help to anchor the stent 102 to prevent migration of the stent 102, without preventing stent removal after implantation. Having the ePTFE layer 106 on the outside of the medical device 100 shown in FIG. 3 can also reduce the friction between a delivery device such as a catheter and the medical device 100 during deployment of the stent into a bodily lumen, which reduces the deployment force required.

Manufacturing the medical device 100, embodiments of which are shown in FIGS. 2-3, requires an application of an elastomeric solution onto one of the inner or outer surfaces of at least one of the ePTFE layer or the stent. In at least one embodiment, the method of manufacturing the medical device comprises the steps of: applying an elastomeric solution to a surface of an ePTFE layer and a surface of a stent; and manipulating the stent-ePTFE assembly by at least one of rotating the stent-ePTFE assembly about an axis and translating the stent-ePTFE assembly relative to an applicator of the elastomeric solution. The elastomeric solution is applied by a process selected from the group consisting of dipping the assembly into the elastomeric solution; spraying the elastomeric solution onto at least one surface of the stent; and inserting the stent-ePTFE assembly into a tube and injecting the elastomeric solution into an injection port of the tube. In some embodiments, the elastomeric solution cures with heat or humidity to form the elastomeric layer.

In some embodiments, the elastomeric solution comprises between about 5 wt. % (weight percent) and about 50 wt. % (weight percent) elastomeric polymer. In some embodiments, the elastomeric solution includes radiopaque particles. In some embodiments, the elastomeric solution includes a therapeutic agent, such as those described above. In some embodiments, the elastomeric solution contains inhibitors to increase shelf life.

In at least one embodiment, the elastomeric solution is a silicone solution. In some embodiments, the silicone solution comprises silicone and a solvent, such as toluene, xylene, and comparable solvents that are compatible with silicone. In some embodiments, the silicone solution comprises between about 5 wt. % (weight percent) and about 50 wt. % (weight percent) silicone. In some embodiments, the elastomeric solution contains elastomeric polymers other than silicone, such as polystyrene-polyisobutylene-polystyrene triblock copolymer (SIBS), polyurethane, and other comparable elastomeric polymers.

In order to manufacture the medical device 100, in some embodiments, a single ePTFE layer 106 is first positioned such that a first surface of the ePTFE layer 106 contacts a first surface of the stent 102. For example, the outer surface 118 of the ePTFE layer 106 contacts the inner surface 112 of the stent 102 (as shown in FIG. 2) or the inner surface 116 of the ePTFE layer 106 contacts the outer surface 114 of the stent 102 (as shown in FIG. 3). An elastomeric solution is then applied to at least a portion of the first surface of the ePTFE layer 106 and at least a portion of the first surface of the stent 102.

In at least those embodiments where the outer surface 118 of the ePTFE layer 104 contacts the inner surface 112 of the stent (or in other words, where the ePTFE layer is deposited within the lumen of the stent as shown in FIG. 2), the elastomeric solution is applied from the outside of the stent 102.

In some embodiments, the ePTFE layer 106 is first placed onto a mandrel and then the stent 102 is placed over the ePTFE layer 106, and the assembly 102, 106 is then coated with the elastomeric solution.

In at least one embodiment, the stent-ePTFE assembly 102, 106 is sprayed with the elastomeric solution. In other embodiments, the stent-ePTFE assembly 102, 106 is dipped into the elastomeric solution. In at least one embodiment, spraying the stent-ePTFE assembly is preferable to dipping the assembly into the elastomeric solution because coating thickness and integrity can be better controlled by spraying the assembly as opposed to dipping the assembly. The coating thickness depends largely upon the viscosity and percent solid of the elastomeric solution. Furthermore, the spraying process requires a smaller quantity of the elastomeric solution than the dipping process.

In some embodiments where the stent-ePTFE assembly 102, 106 is sprayed with the elastomeric solution, the elastomeric solution comprises between about 5 wt. % (weight percent) and about 20 wt. % (weight percent) elastomeric polymer. In some embodiments where the stent-ePTFE assembly 102, 106 is dipped into the elastomeric solution, the elastomeric solution comprises between about 15 wt. % (weight percent) and about 25 wt. % (weight percent) elastomeric polymer.

In at least one embodiment, the elastomeric solution is 10 wt. % silicone elastomer (such as NuSil MED-4820) and 90 wt. % toluene. In at least one embodiment, the elastomeric solution is 20 wt. % silicone elastomer (such as NuSil MED-4820) and 80% wt. % xylene. Other solutions may be used Inhibitors and primers can also be added to the elastomeric solution.

Figure 4:
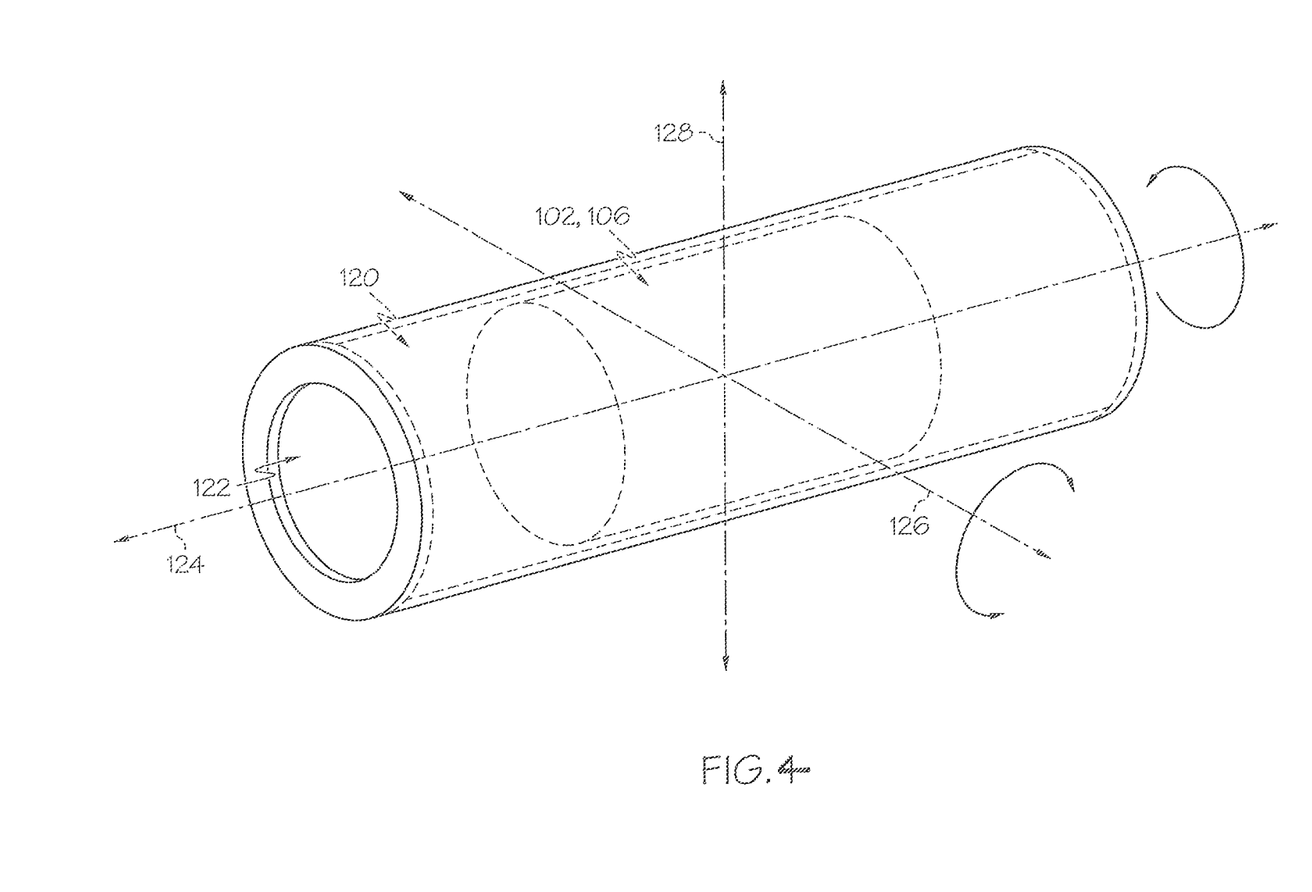
FIG. 4 is a schematic view that shows an apparatus used for injecting the elastomeric solution into the stent-ePTFE assembly.

In at least those embodiments where the inner surface of the ePTFE layer contacts the outer surface of the stent (or in other words, where the stent is deposited within the lumen of the ePTFE layer as shown in FIG. 3), the elastomeric solution is applied from the inside of the stent. In at least one embodiment, the stent-ePTFE assembly 102, 106 is placed inside of a tube 120, as shown in FIG. 4. In at least one embodiment, the tube 120 has an injection port 122 for injecting the elastomeric solution into the stent-ePTFE assembly. A mechanism can be used to allow the tube 120 to be rotated about at least one of the longitudinal axis 124 and a second axis 126 to spread the injected elastomeric solution along a surface of the stent, the ePTFE layer, or both. In at least one embodiment, the rotation of the tube 120 is uniform, which allows for uniform application and adhesion of the elastomeric solution. In at least one embodiment, the tube 120 can be rotated by hand about at least the longitudinal axis 124 and the second axis 126 after the elastomeric solution has been injected into the tube 120. The rotating or tilting motion allows the elastomeric solution to sufficiently cover portions of the stent-ePTFE assembly such that when the elastomeric solution cures, the stent is adhered to the ePTFE layer. In some embodiments, the elastomeric solution covers at least a portion of the interior surface of the ePTFE layer and at least a portion of the stent.

In at least one embodiment, the tube 120 containing stent-ePTFE assembly 102, 106 can be rotated about the longitudinal axis 124, a second axis 126 that is perpendicular to the longitudinal axis 124, a third axis 128 that is perpendicular to both the longitudinal axis 124 and the second axis 126, and combinations thereof. In at least one embodiment, the tube 120 with the stent-ePTFE assembly 102, 106 can be translated along the longitudinal axis 124, along the second axis 126, and/or along the third axis 128. The tube 120 can be rotated and/or translated about any of the axes 124, 126, 128 in any desired combination.

In other embodiments, the stent-ePTFE assembly can be dipped into the elastomeric solution and manipulated by rotating and/or tilting the assembly such that the elastomeric solution covers at least a portion of a surface of the ePTFE layer and at least a portion of the stent. In some embodiments where the stent-ePTFE assembly 102, 106 is dipped into the elastomeric solution, the elastomeric solution comprises between about 15 wt. % (weight percent) and about 25 wt. % (weight percent) elastomeric polymer. In at least one embodiment, the stent-ePTFE assembly can be rotated and/or tilted about the longitudinal axis 124, a second axis 126 that is perpendicular to the longitudinal axis 124, a third axis 128 that is perpendicular to both the longitudinal axis 124 and the second axis 126, and combinations thereof. In at least one embodiment, the stent-ePTFE assembly can also be placed inside the tube 120 and then dipped into the elastomeric solution.

Figure 5:
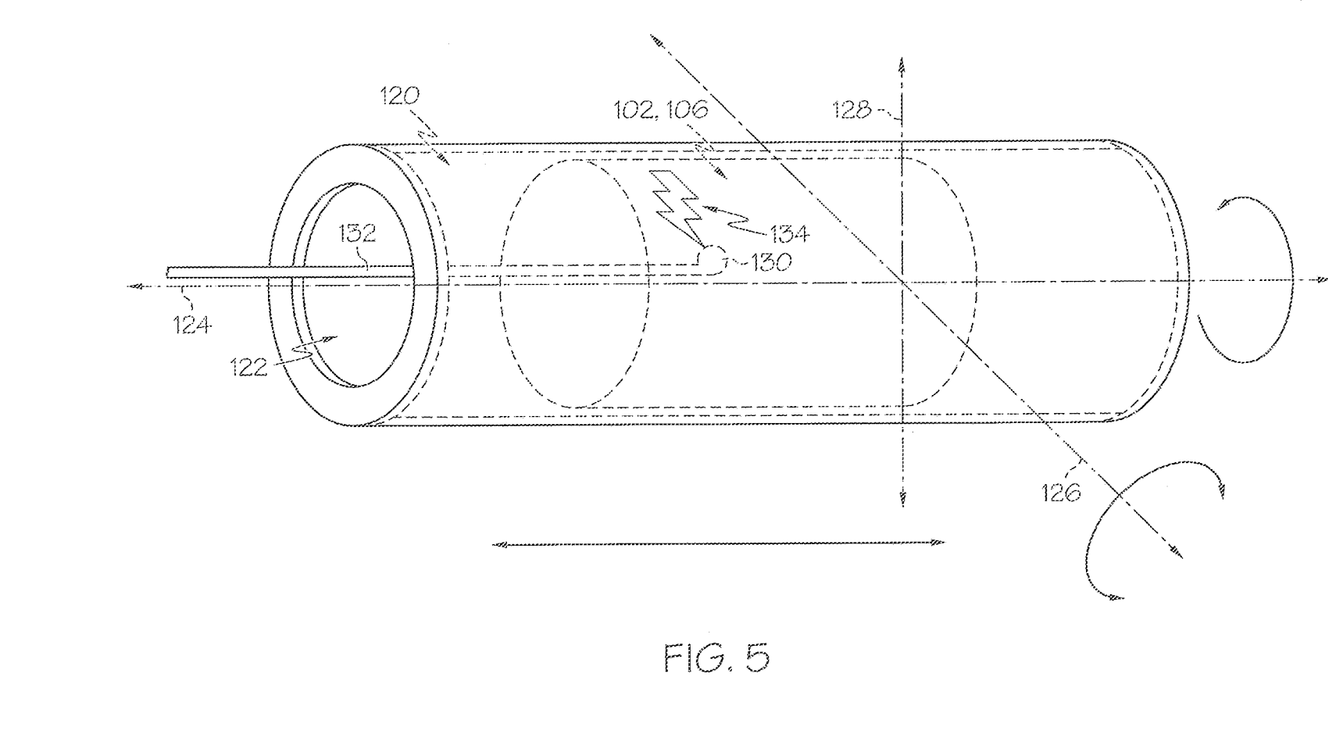
FIG. 5 is a schematic view that shows an apparatus used for spraying the elastomeric solution onto the stent-ePTFE assembly.

In another embodiment shown in FIG. 5, a nozzle 130 mounted onto a bar 132 can be inserted into the lumen of the stent-ePTFE assembly 102, 106 and the elastomeric solution can be sprayed (shown at 134) onto at least a portion of the ePTFE layer and the stent. The nozzle 130 mounted onto the bar 132 can be rotated or translated or the stent-ePTFE assembly can be rotated or translated such that the stent-ePTFE assembly moves relative to the nozzle and a desired portion of the stent-ePTFE assembly can be covered with the elastomeric solution. In some embodiments where the stent-ePTFE assembly 102, 106 is sprayed with the elastomeric solution, the elastomeric solution comprises between about 5 wt. % (weight percent) and about 20 wt. % (weight percent) elastomeric polymer.

As discussed above, the stent-ePTFE assembly 102, 106 can be rotated about the longitudinal axis 124, a second axis 126 that is perpendicular to the longitudinal axis 124, a third axis 128 that is perpendicular to both the longitudinal axis 124 and the second axis 126, and combinations thereof. In at least one embodiment, the stent-ePTFE assembly 102, 106 can be translated along the longitudinal axis 124, along the second axis 126, and/or along the third axis 128. The stent-ePTFE assembly 102, 106 can be rotated and/or translated about any of the axes 124, 126, 128 in any desired combination. The nozzle 130 can also be rotated about its longitudinal axis, a second axis that is perpendicular to its longitudinal axis, and a third axis that is perpendicular to both its longitudinal axis and the second axis. In at least one embodiment, the stent-ePTFE assembly 102, 106 can be rotated and/or translated simultaneously with the nozzle 130.

In at least one embodiment, as shown in FIG. 5, the stent-ePTFE assembly 102, 106 can be inserted into the tube 120 with the injection port 122. The nozzle 130 mounted onto the bar 132 can be inserted into the injection port 122.

As discussed above, in some embodiments, the stent-ePTFE assembly 102, 106 is sprayed with the elastomeric solution using a nozzle 130. In at least one embodiment, shown in FIG. 6, a spray system 140 is provided that comprises a syringe 142, a gas supply 144, and a nozzle 130. The syringe 142 and the gas supply 144 are each connected to the nozzle 130 with tubing 146, 148, respectively. The elastomeric solution is loaded into the syringe 142, which is placed into an automated syringe pump (not shown). The automated syringe pump allows for precise control of the amount of elastomeric solution that is applied to the stent. The syringe 142 connects to the nozzle 130 with tubing 146, and the nozzle 130 is also connected to a gas supply 144 with tubing 148. In one embodiment, the elastomeric solution is mixed with a gas from the gas supply 144 in the nozzle 130 to create a spray 134. In at least one embodiment, the gas supplied to the spraying nozzle 130 can be selected from the group consisting of air and nitrogen. In at least one embodiment, the gas is pressurized at between about 10 psi and 15 psi.

Figure 6:
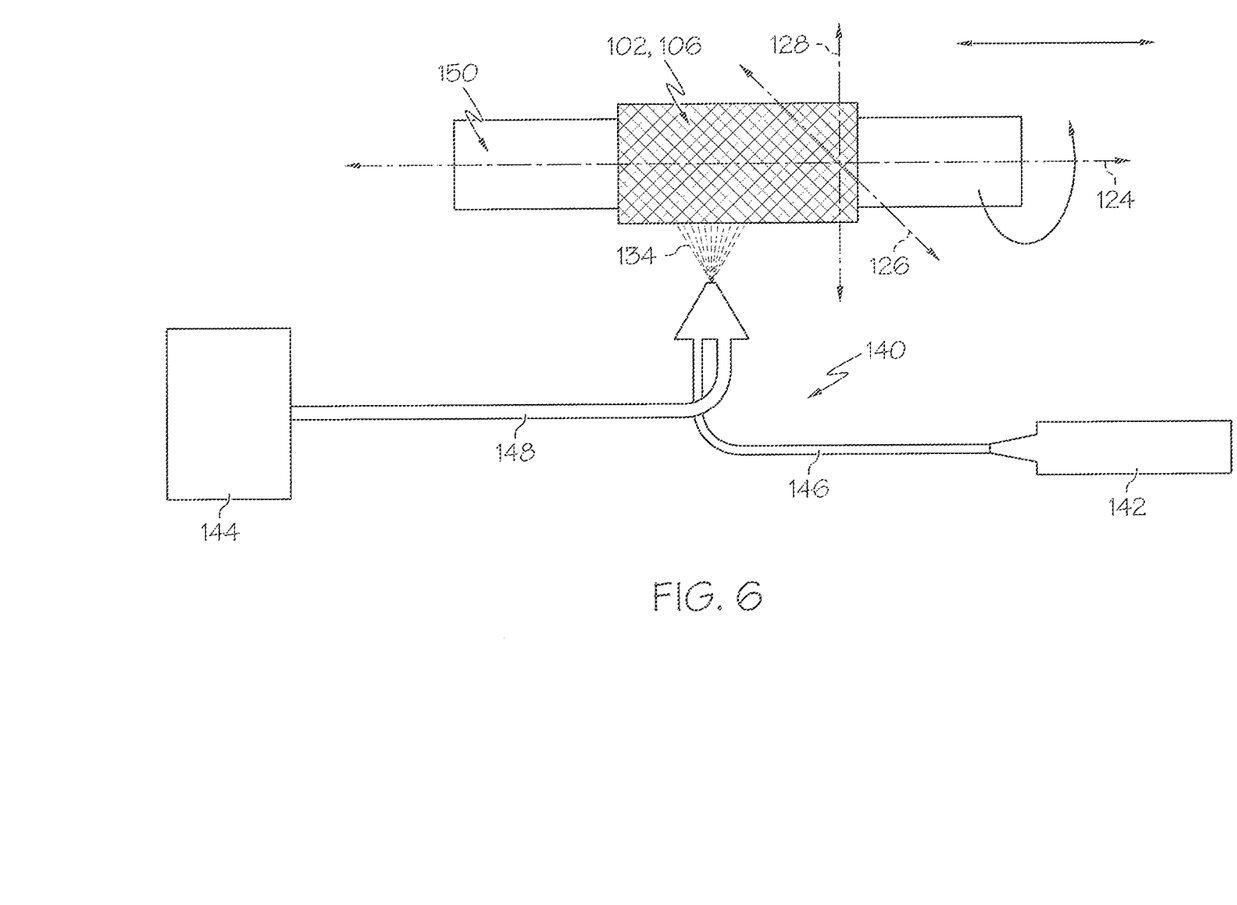
FIG. 6 is a schematic view that shows an apparatus used for spraying the elastomeric solution onto the stent-ePTFE assembly.

As discussed above, depending on whether the stent contacts the outer surface of the ePTFE layer or the inner surface of the ePTFE layer, the nozzle can be inserted into the lumen of the stent-ePTFE assembly 102, 106 to spray the inside surface as shown in FIG. 5 or can spray the outside surface of the stent-ePTFE assembly as shown in FIG. 6. Additionally, as shown in FIG. 6 and previously discussed above, the stent-ePTFE assembly 102, 106 can be placed onto a mandrel 150, which can be rotated or translated relative to the nozzle or the nozzle can be rotated or translated relative to the mandrel. In at least one embodiment, the elastomeric solution can be applied via the mandrel 150 by conveying the elastomeric solution through a lumen of the mandrel 150 and into openings in the surface of the mandrel, where the elastomeric solution can contact the stent-ePTFE assembly 102, 106.

In one embodiment, the flow rate of the elastomeric solution when sprayed is about 150 mL/hour. In at least one embodiment, the amount of applied elastomeric solution is between about 20 mL and 40 mL. In at least one embodiment, the stent-ePTFE assembly moves relatively to the nozzle head at a speed of about 5 mm/sec. In at least one embodiment, the stent-ePTFE assembly rotates relatively to the nozzle head at a speed of about 45 rpm.

In at least one embodiment, an electrostatic spraying system can be used. An electric field can be applied between the nozzle and the stent to improve the coating application.

In at least one embodiment, where a partially covered stent is desired, a portion of the stent can be masked during the spraying process with a shield or the undesired portion of the elastomeric layer can be removed later (either prior to curing or in some cases after curing).

In some embodiments, the thickness of the elastomeric layer is uniform. In other embodiments, the thickness of the elastomeric layer is non-uniform. In at least one embodiment, the thickness of the elastomeric layer can be increased or decreased on the stent depending on the desired radial force of the stent, particularly in the central region of a flared stent as opposed to the flares of the flared stent.

As discussed above, in some embodiments, a mandrel 150 can be used during the coating process. In at least one embodiment, the mandrel 150 is made out of PTFE or another material with a very low coefficient of friction that allows for easy removal of the assembly after coating. In some embodiments, it may be desirable to use a collapsible mandrel, particularly where the stent 102 has a non-uniform diameter. In such embodiments, the mandrel 150 may comprise a balloon. In at least one embodiment, the balloon has waste portions between the proximal end and the distal end and a central portion between the waste portions. A deflated balloon is inserted inside the lumen of the stent and inflated to conform to the shape of the stent.

In at least one embodiment, the balloon is pre-shaped to conform to the shape of the stent. In at least one embodiment, the balloon is sized relative to the size of the stent. In some embodiments, the balloon has a constant diameter in the central portion of the balloon when fully expanded. In other embodiments, the balloon has a non-constant diameter in the central portion of the balloon when fully expanded.

The elastomeric solution can then be applied over the stent and balloon. In at least one embodiment, the ePTFE layer is placed over the stent and the applied elastomeric solution is allowed to cure. In some embodiments, the elastomeric solution cures with heat or humidity. Once it is cured, the balloon is deflated and removed from the interior of the stent.

In some embodiments, a rod made from a metal or polymer can be inserted into the lumen of the balloon to rigidify the assembly. This rod can also include holes to facilitate balloon inflation.

The balloon can be either for single use or for multi-use applications. The balloon can be a compliant, semi-compliant or non-compliant balloon. In some embodiments, the balloon is made out of various polymers such as nylon, PET, polyurethane, and other such materials. In some embodiments, the balloon has a single layer of material. In other embodiments, the balloon has more than one layer of material. In at least one embodiment, an outer layer of the balloon can comprise PTFE. In at least one embodiment, an outer layer of the balloon can be designed to facilitate removal of the stent from the balloon. In some embodiments, the outer layer of the balloon can have bumps, ribs, ridges, and other surface features that reduce surface contact. In at least one embodiment, the balloon can be coated with a mold release agent or any other agent that facilitates the release of the stent (including, but not limited to, waxes and oils).

In at least one embodiment, at least one layer of ePTFE can be placed between the balloon and the stent. In at least one embodiment, at least one layer of a substance such as Teflon can be placed between the balloon and the stent.

The balloon can be inflated with a pressurized medium such as a liquid or a gas. In at least one embodiment, the balloon can be inflated with an inflator that maintains a constant pressure to accommodate changes in temperature.

In any of the methods described above, the elastomeric layer 104 can be applied in a single layer or in multiple layers. In at least one embodiment, the medical device 100 has more than one layer of ePTFE.

In at least one embodiment, the medical device 100 includes a primer layer between the elastomeric layer 104 and the stent layer 102. In at least one embodiment, the primer layer comprises a primer material such as NuSil MED-160 or other suitable materials. The primer layer may improve the adhesion of the elastomeric layer 104 to the stent layer 102. In at least one embodiment, the primer material is applied directly to the stent layer 102 either by spraying the material onto the stent or dipping the stent layer into the material using techniques such as the techniques described above with respect to the application of the elastomeric material.

This completes the description of the preferred and alternate embodiments of the invention. Those skilled in the art may recognize other equivalents to the specific embodiment described herein, the equivalents of which are intended to be encompassed by the claims attached hereto.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

The invention claimed is:

1. A method of making a stent-graft, the method comprising the steps of:
    providing a tube of ePTFE having an inner surface defining an inner lumen and an outer surface;
    disposing a stent within the inner lumen of the ePTFE tube to form an ePTFE-stent assembly, the stent comprising an inner surface defining a lumen and an outer surface, the ePTFE-stent assembly having an inner lumen; and
    applying an elastomeric solution into the inner lumen of the ePTFE-stent assembly, wherein the ePTFE-stent assembly is manipulated during applying of the elastomeric solution by rotating the ePTFE-stent assembly about an axis and translating the ePTFE-stent assembly relative to an applicator of the elastomeric solution.

2. The method of claim 1 further comprising rotating the ePTFE-stent assembly uniformly to allow for a uniform application of the elastomer solution.

3. The method of claim 1 further disposing the ePTFE-stent assembly in a tube.

4. The method of claim 3 further comprising inserting a nozzle into the tube and into the inner lumen of the ePTFE-stent assembly and injecting the elastomeric solution through the nozzle.

5. The method of claim 4 wherein the nozzle is a spray nozzle.

6. The method of claim 5 wherein the spray nozzle comprises a syringe and a gas supply, the syringe and the gas supply connected to the nozzle, the elastomeric solution is loaded into the syringe, the syringe is further connected to an automated pump, the elastomeric solution is mixed with gas from the gas supply.

7. The method of claim 2 wherein rotating the ePTFE-stent assembly comprises rotating the ePTFE-stent assembly about a longitudinal axis of the tube and about a second axis.

8. The method of claim 7 wherein rotating the ePTFE-stent assembly further comprises rotating the ePTFE-stent assembly about a third axis.

9. The method of claim 7 wherein the second axis is perpendicular to the first axis.

10. The method of claim 9 wherein the third axis is perpendicular to both of the first axis and the second axis.

11. The method of claim 1 wherein the elastomeric solution comprises about 5 wt-% to about 20 wt-% of an elastomeric polymer and 95 wt-% to about 80 wt-% solvent.

12. The method of claim 11 wherein the elastomeric solution comprises about 10 wt-% to about 20 wt-% of the elastomeric polymer.

13. The method of claim 11 wherein the elastomeric polymer comprises at least one member selected from the group consisting of silicone, polystyrene-polyisobutylene-polystyrene triblock copolymer (SIBS) and polyurethane.

14. The method of claim 11 wherein the solvent is toluene or xylene.

15. The method of claim 11 wherein the elastomeric solution comprises about 5 wt-% to about 50 wt-% silicone.

16. The method of claim 11 wherein the elastomeric solution comprises about 10 wt-% silicone and about 90 wt-% toluene.

17. The method of claim 11 wherein the elastomeric solution comprises about 20 wt-% silicone and about 80 wt-% xylene.

18. The method of claim 1 wherein the elastomeric solution further comprises a therapeutic agent.

19. The method of claim 1 wherein the elastomeric solution further comprises inhibitors or primers.

20. The method of claim 1, wherein the single ePTFE layer has a wall thickness between about 25 microns (0.001 in) and 500 microns (0.020 in).

* * * * *